United States Patent [19]

Lenski et al.

[11] Patent Number: 4,663,978
[45] Date of Patent: May 12, 1987

[54] CLEAN GRAIN SAMPLER FOR A COMBINE HARVESTER

[75] Inventors: Ralph Lenski; Harald Quoiffy, both of Zweibrücken, Fed. Rep. of Germany

[73] Assignee: Deere & Company, Moline, Ill.

[21] Appl. No.: 794,825

[22] Filed: Nov. 1, 1985

[30] Foreign Application Priority Data

Nov. 7, 1984 [EP] European Pat. Off. ........ 84113448.9

[51] Int. Cl.⁴ ............................................. G01N 1/20
[52] U.S. Cl. .............................. 73/863.52; 73/863.55; 73/863.43; 73/863.81; 130/27 R
[58] Field of Search ........... 73/863.52, 863.55, 863.43, 73/863.57, 863.81, 863.53, 864.51, 864.63; 130/27 R

[56] References Cited

U.S. PATENT DOCUMENTS

| | | | |
|---|---|---|---|
| 3,474,675 | 10/1969 | Strond | 73/863.55 |
| 3,735,641 | 5/1973 | Bink et al. | 73/863.52 X |
| 4,026,155 | 5/1977 | Joseph | 73/863.55 |
| 4,393,704 | 7/1983 | Bortko | 73/863.52 X |
| 4,574,645 | 3/1986 | Allen et al. | 73/863.81 X |

Primary Examiner—Stewart J. Levy
Assistant Examiner—Tom Noland

[57] ABSTRACT

In a self-propelled combine harvester, a grain sampling device is inserted in an opening in the common wall structure shared by the rear of the operator enclosure and the front of the grain tank. In the opening, a prism shaped receiving cup rocks about its bottom edge between a closed position in which the cup extends into the tank and the wall opening is sealed; an intermediate position in which grain is collected in the cup; and a third position in which the opening is again sealed and the cup extends into the operator enclosure, permitting extraction of the grain sample from the cup. A chute diverts a portion of the delivery of grain from the clean grain elevator to the sampling cup so that grain may be sampled at all states of filling of the grain tank.

10 Claims, 3 Drawing Figures

CLEAN GRAIN SAMPLER FOR A COMBINE HARVESTER

BACKGROUND OF THE INVENTION

The invention concerns an arrangement for sampling the grain being delivered to the grain tank of a combine harvester and more particularly, one which is usable and accessible from the operator station of the combine.

It is already known, in combine harvesters in which the operator's station is adjacent a wall of the combine's grain tank, to provide a flap or door hinged along its top edge, permitting the operator to reach into the grain tank to obtain a sample of grain. However, this arrangement permits sampling only when the level of grain in the tank is at or above levels reachable by the operator. In addition, use of a simple access flap of this type requires that it be open for a significant length of time which, when used with operator enclosure atmosphere conditioning equipment involving pressurizing of the enclosure, results in an undesirable loss of air and pressure and the possibility of dust and debris entering the enclosure.

SUMMARY OF THE INVENTION

Accordingly, an object of the invention is to provide in a combine harvester in which the harvester operator's station is adjacent a wall of the grain tank a clean grain sample receiver mounted in or communicating with the adjacent wall of the grain tank and movable between a normally closed and inoperative position and a sample presentation position in both of which communication between the operator's station and the grain tank remains closed or sealed.

A further object of the invention is to provide means for delivering grain to the sample receiver such that grain may be conveniently sampled over a wide range of fill levels of the grain tank.

In keeping with the invention, means may be provided for diverting at least a portion of the flow of clean grain delivered to the tank into the vicinity of the sampling device so that when the sampler is appropriately set, grain may be received by it. Preferably, the sampler receiver is in the form of a cup or funnel opening generally upwards and having an inner wall and an outer wall and mounted in an opening or orifice of the grain tank wall so as to pivot about a lower edge of the receiver. The receiver may be arranged to have three significant positions, including: (a) a closed position in which the receiver is pivoted inwards and so inclined that it cannot retain any grain impinging upon it and in which the outer wall substantially closes the opening in the tank wall, (b) a receiving or sampling position in which the inner wall remains disposed inwardly of the opening in the tank wall and the outer wall is spaced outwardly of the opening and the receiver is disposed generally upright so that grain entering it is retained by the receiver, and (c) a delivery position in which the receiver has been pivoted outwardly from the orifice or opening in the grain tank wall and the opening is once again closed, but this time, by the inner wall engaging the opening in the tank wall.

It is an advantage of a grain sampling device according to the invention, that the diversion of grain from the grain tank filling device for potential collection by the sample receiver makes it possible to sample the incoming grain at substantially all levels of fill of the grain tank.

DESCRIPTION OF THE PREFERRED EMBODIMENT

Figure 1:
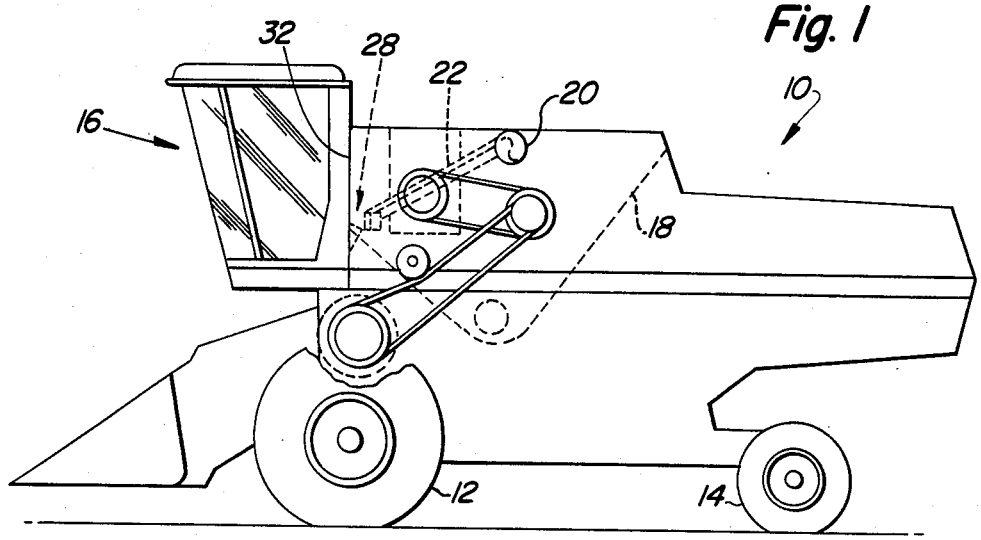
FIG. 1 is a left-hand, semi-schematic side elevation of a self-propelled combine harvester embodying the invention.

The invention is embodied in an otherwise conventional, self-propelled combine 10, as shown in FIG. 1. The combine is supported on a pair of driven front wheels 12 and steerable rear wheels 14. Immediately behind the operator's station 16 is a grain tank for receiving clean grain after processing by the separating mechanisms and diverted to it by a clean grain conveyor system indicated only partially by the exemplary screw conveyor 20 shown in FIG. 2. At least some of the grain from the screw conveyor 20 is diverted into a chute 22 assisted by a deflector 26. The discharge from the chute 22 is directed towards a sampling device 28 which is supported in an opening 52 in an upright bulkhead or wall 32 which may be a common bulkhead serving as a rear wall of the operator enclosure or cab and a front wall of the grain tank 18. The receiving cup 30 is formed of approximately, mutually perpendicular outer and inner walls 34 and 36, respectively, and quadrant-shaped opposite side walls or end walls 38, each of which is notched at 39. The width of the cup 30 is approximately equal to its depth and it is pivotably supported adjacent the lower edge of the orifice 52 in the wall 32.

The outer and inner walls 34, 36, respectively, of the receiving cup 30 meet at a bead or bearing member 41 extending the full width of the cup between the opposite side walls 38.

An adapter frame or carrier 44 is inserted in the opening 52 and provides support for the receiving cup 30. The frame 44 is attached to the wall 32 by suitable hardware 47 and includes a peripheral flange 46 and a hood extending into the grain tank and comprising a "roof" member 48 and opposite side walls 49.

The bottom edge 43 of the frame member 44 extends a short distance into the grain tank and includes an upwardly turned lip helping to position the bead 41 of the cup 30. The cup 30 is thus pivotably contained within and fills the frame 44 and is rockable on the bead 41 between a closed and inoperative position, indicated at A in FIG. 2, in which sealing or closing of the opening 52 is improved by the engagement of the upper edge 62 of the outer wall 34 with a gasket 50 carried by a hood or web 48 and a delivery position C, indicated in phantom outline in FIG. 2, in which the wall opening 52 is again closed and sealing is assisted by the engagement of a gasket 56 carried by the top edge of the cup inner wall 36 engaging an edge of the hood 48. In all positions, a close fit between the cup walls 38 and the hood walls 49 helps to maintain closure of the opening 52. Manipulation of the cup 30 is facilitated by a molded handle 60 of the outer wall 34 of the cup.

Figure 2:
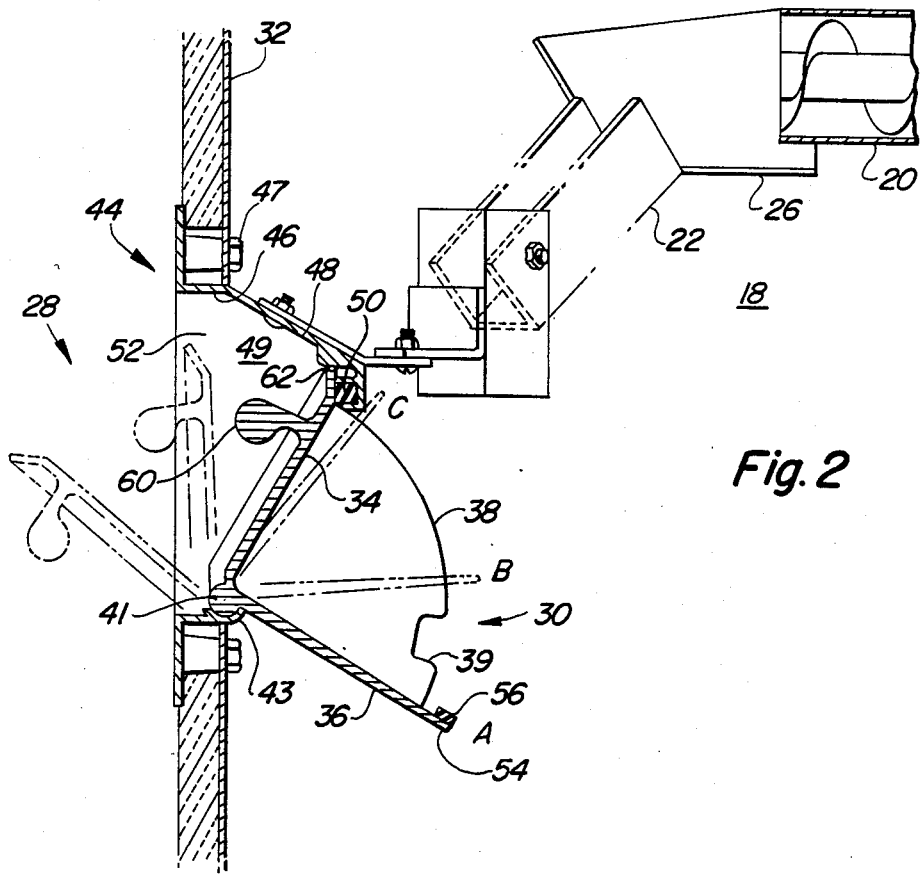
FIG. 2 is an enlarged, somewhat schematic view, including a cross-sectional view on a vertical plane passing through the opening in the grain tank and showing the chute used to divert incoming grain to the sampler.
Figure 3:
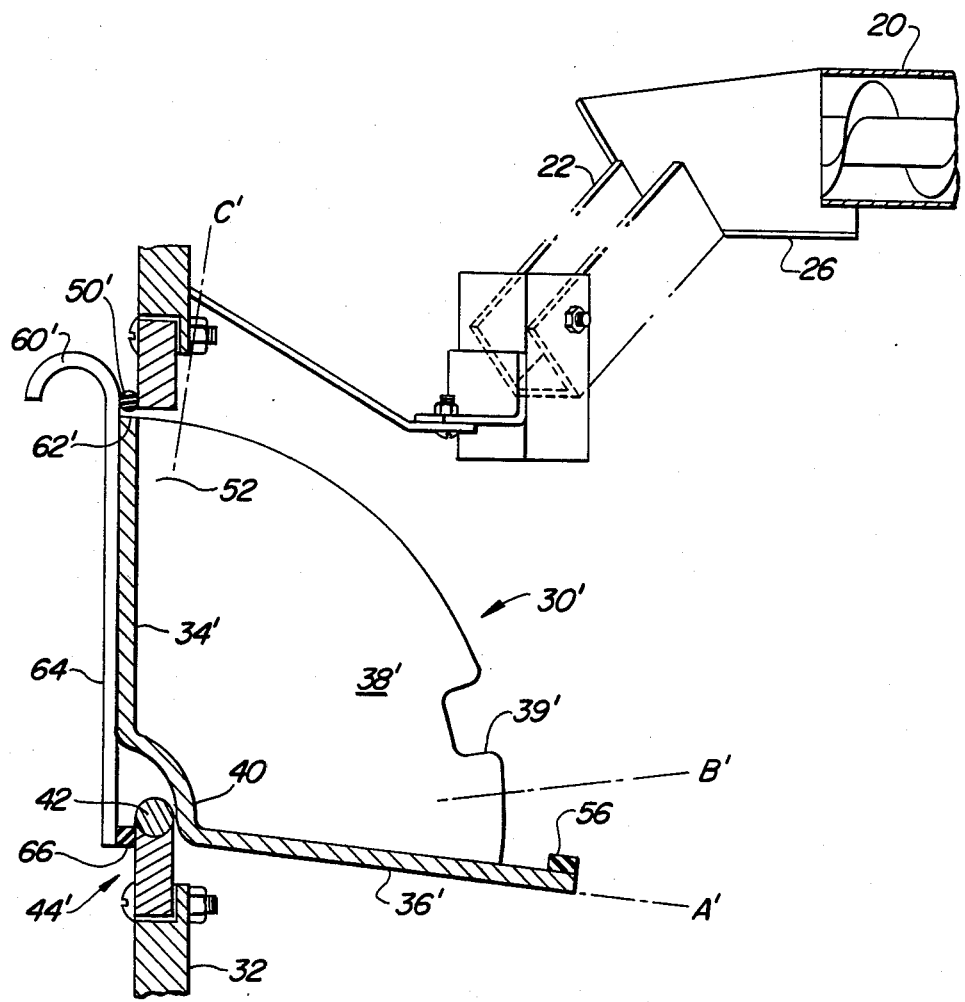
FIG. 3 is a view similar to FIG. 2 of an alternative embodiment of the invention.

In the alternative and rather simpler embodiment of FIG. 3, a simple frame 44' replaces the hooded frame 44 of FIG. 2. Pivot bearing is provided by an indentation 40 in the cup 30' bearing on a bead 42 extending along the bottom edge of the frame 44'. In this case, in the closed or inoperative position, the sealing of the opening 52 is assisted by a gasket 50' carried by the upper edge 62' of the outer wall 34' of the cup 30', bearing against an external surface of the frame 44'. The outer wall 34' is faced by a sheet metal cover 64 which is formed into a handle 60' at its upper edge and extends downwards beyond the bead 42 and carries at its lower edge an additional gasket 66 bearing on the lower edge of the frame 44'.

In operation, and referring particularly to the embodiment of FIG. 2, the receiving cup 30 is normally closed and inactive (position A) and dust and grain is prevented from entering the operator enclosure 16. The angle of inclination of the inner wall 36 of the cup 30 is such that, although during harvesting and the continuous delivery of grain into the tank, with some of the grain being diverted by the chute 22 towards the cup 30, no grain collects in the cup because the angle of inclination of inner wall 36 is about equal to or greater than the angle of repose of the grain. However, if desired, grain may be sampled at any stage of filling of the tank if the operator, assisted by the handle 60, moves cup 30 into the intermediate position B in which grain can be collected in the cup 30. Movement of the cup into position C again seals the opening between grain tank and operator enclosure and the grain sample may be removed from the cup and inspected at leisure. Clearly, in normal operation, a grain sample of adequate size may be collected in a very short time so that the opening 52 in the tank and operator enclosure wall is open for only a very short time and movement of air between enclosure and tank and entry of dust into the enclosure is minimized. After inspection, and if desired, the grain sample may be returned to the tank by replacing it in the cup 30 and returning the cup to position A.

The operation of the embodiment of FIG. 3 is similar except that here, the configuration of the cup and frame arrangement is such that the inner wall 36' provides, in the closed position A, a platform on which the grain sample is constantly replenished under the flow of grain from the chute 22 so that the act of moving the cup between the closed and inoperative position A and the extraction and second closed position C' requires only a momentary pause, if any, in an intermediate position B' to ensure that an adequate sample is collected.

From the drawings and the above description, it is clear that in both embodiments, a sub-assembly of the support frame (44, 44') and the sample or receiving cup (30, 30') may be made and inserted into the wall opening 52 and secured by suitable hardware. Once installed, the construction is such that the individual cups 30, 30' may be disassembled from their support frames by moving them into an intermediate position and lifting them upwards so as to disengage the pivot bearing members (41, 43 and 40, 42, respectively) assisted by the clearance provided by the notches (39, 39') in the side walls (38, 38') of the cup.

We claim:

1. In a combine harvester having an operator's station and a grain tank including a generally upright wall, a forward crop gatherer, and means for threshing and separating the gathered crop into clean grain, straw and chaff fractions, and means for delivering the clean grain fraction to a delivery point adjacent the tank, an improved clean grain sampling arrangement comprising:
   an aperture in the tank wall; and
   a receiving cup having an opening/and pivotably supported in the aperture and movable between an inactive position and a sample presenting position and wherein in both positions, the aperture is closed by the receiving cup.

2. The sampling arrangement of claim 1 wherein the cup is pivotable into an intermediate clean grain receiving position where the aperture is open so there is communication between the inside and the outside of the tank.

3. The sampling arrangement of claim 1 and further including means for diverting at least a portion of the clean grain delivery from the delivery point to the receiving cup.

4. The sampling arrangement of claim 3 wherein the means for diverting comprises a chute having a receiving end adjacent the delivery point and a discharge end adjacent the receiving cup.

5. The sampling arrangement of claim 1 wherein the aperture has a lower edge and the cup engages the lower edge and is thereby pivotably supported for rocking movement about an axis parallel to the lower edge between the inactive position in which the cup opening is directed into the tank and the sample presenting position in which the cup opening is directed generally upwardly and externally of the tank wall.

6. The sampling arrangement of claim 5 wherein the receiving cup includes spaced-apart inner and outer walls and said walls are disposed so that in the inactive position, the aperture is closed by the outer wall and in the sample presenting position, the aperture is closed by the inner wall.

7. The sampling arrangement of claim 5 wherein in the inactive position, the cup opening is directed into the tank and the inner wall is inclined generally downwardly so that grain entering the cup is not retained by it.

8. The sampling arrangement of claim 5 wherein the cup includes a contoured member engaging the lower edge of the aperture and said engagement defines the pivot axis for rocking motion of the cup.

9. The sampling arrangement of claim 8 wherein the contoured member is a bead of generally circular cross-section and wherein the lower edge of the aperture is recessed to receive said bead.

10. The sampling arrangement of claim 1 and further including a frame for mounting in the aperture and supporting the cup and wherein said frame includes stop surfaces for engaging inner and outer walls of the cup and defining the sample presenting and inactive positions, respectively, and for defining a lower edge of the aperture for engaging and supporting a lower portion of the cup.

* * * * *